United States Patent [19]

Greenley et al.

[11] Patent Number: 5,407,569
[45] Date of Patent: Apr. 18, 1995

[54] MOBILE PHASE RESERVOIR

[75] Inventors: Larry V. Greenley, Vienna, Va.; V. Cloud Volpe, Vineland, N.J.

[73] Assignee: SP Industries Ltd. Partnership, Miami, Fla.

[21] Appl. No.: 129,269

[22] Filed: Sep. 30, 1993

Related U.S. Application Data

[62] Division of Ser. No. 909,575, Jul. 6, 1992, Pat. No. 5,275,723.

[51] Int. Cl.$^6$ .............................................. B01D 15/08
[52] U.S. Cl. ................................. 210/198.2; 210/101; 210/541; 210/656; 366/279
[58] Field of Search ............... 210/635, 656, 101, 541, 210/198.2; 366/241, 279, 280, 282, 349; 206/219, 305

[56] References Cited

U.S. PATENT DOCUMENTS

| | | | |
|---|---|---|---|
| D. 292,824 | 11/1987 | Babashak | D24/8 |
| 3,481,712 | 12/1969 | Bernstein et al. | 23/292 |
| 3,830,369 | 8/1974 | Pfadenhauer | 210/198.2 |
| 3,934,456 | 1/1976 | Munk | 210/198.2 |
| 4,116,046 | 9/1978 | Stein | 210/198.2 |
| 4,496,245 | 1/1985 | Conrad | 210/198.2 |
| 4,591,422 | 5/1986 | Andrews | 210/198.2 |
| 4,879,029 | 11/1989 | Whitehead | 210/198.2 |
| 4,954,253 | 9/1990 | Alexandrov | 210/198.2 |
| 4,960,516 | 10/1990 | Alexandrov | 210/198.2 |
| 5,080,784 | 1/1992 | James | 210/198.2 |
| 5,089,124 | 2/1992 | Mahar | 210/198.2 |
| 5,158,675 | 10/1992 | Allington | 210/198.2 |

OTHER PUBLICATIONS

Chromware HPLC Mobile Phase Handling Systems, Nov. 3, 1991, Lab Glass Biotechnology Products, Vineland, N.J. pp. 1-20.

Primary Examiner—Ernest G. Therkorn
Attorney, Agent, or Firm—Arnold, White & Durkee

[57] ABSTRACT

The present invention relates to a reservoir for storage and use of the liquid or mobile phase of a liquid chromatography system. The reservoir comprises a main chamber for containing the majority of the mobile phase and having a conical base with two apertures and two cavities subtending the apertures and in fluid communication with the main chamber. These cavities are adapted to receive a stirrer and a pump filter and to maintain these devices separate from each other during operation. The structure of the reservoir provides for more rapid and thorough mixing and virtually complete utilization of the mobile phase while minimizing introduction of gaseous phase into the liquid chromatography system downstream from the reservoir.

15 Claims, 3 Drawing Sheets

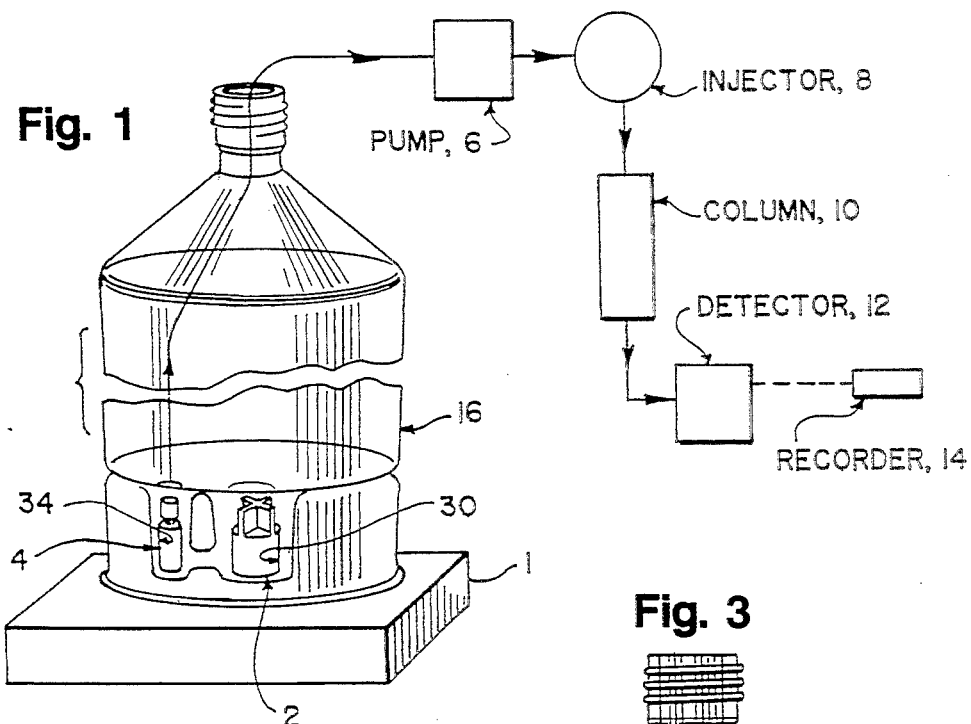
Fig. 1
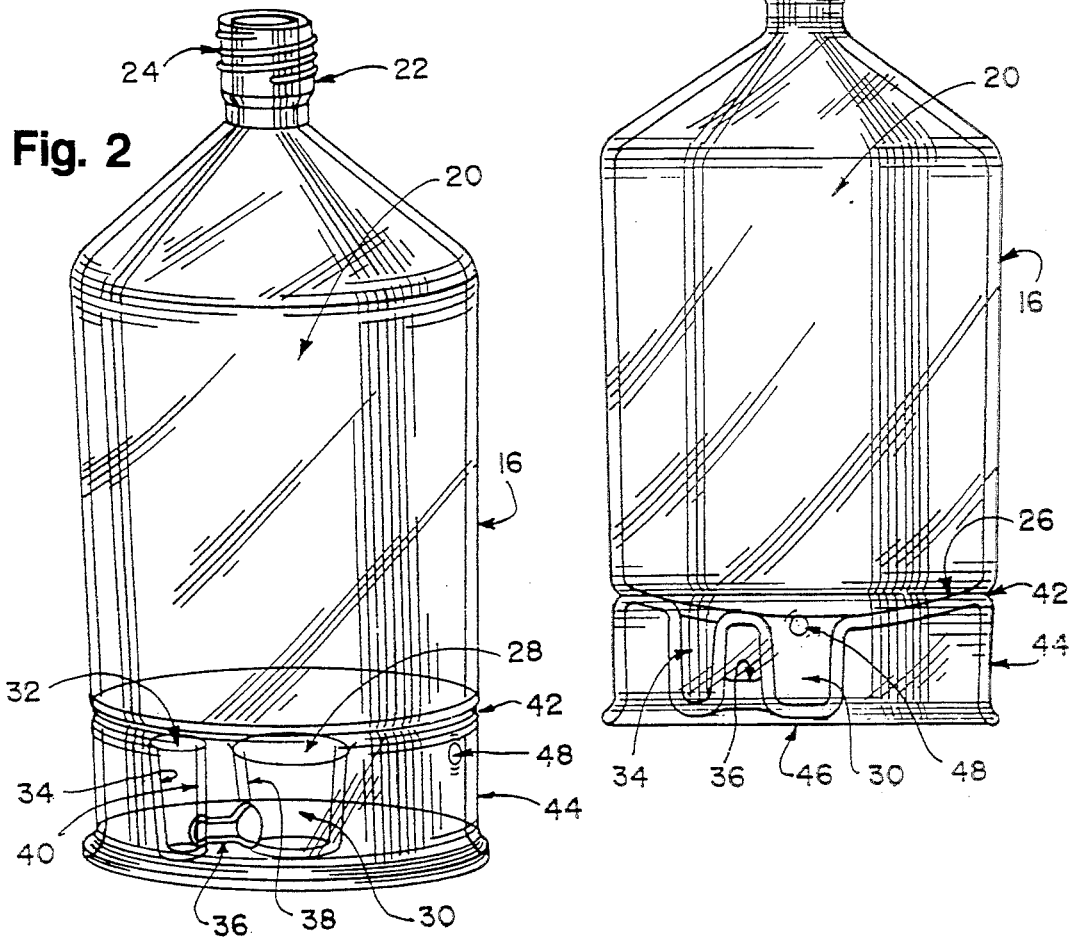
Fig. 2
Fig. 3

MOBILE PHASE RESERVOIR

CROSS-REFERENCE TO RELATED APPLICATIONS

This application is a divisional of application Ser. No. 07/909,575, filed Jul. 6, 1992, now U.S. Pat. No. 5,275,723.

FIELD OF THE INVENTION

The present invention relates to the structure of a reservoir for use in a liquid chromatography system, and particularly a reservoir for holding and mixing the liquid or mobile phase of a high performance liquid chromatography system.

BACKGROUND OF THE INVENTION

In its most general sense chromatography is the separation of mixtures of chemical substances into their component parts by chromatographic adsorption for analytical purposes. Chromatographic adsorption is the preferential adsorption or differential retention of chemical compounds on the basis of molecular size, charge, hydrophobicity or biospecific affinity by an adsorbent material. Liquid chromatography is a form of chromatography using a liquid as the mobile phase and a solid or a liquid on a solid support as the stationary adsorbent phase. A liquid chromatography system typically includes at least the following elements which are connected together in a manner well known to those of ordinary skill in the field: a reservoir, a pump, an injector, a column, a detector, and a recorder. High performance liquid chromatography ("HPLC") utilizes specific modifications in the design and nature of the column, the column material, the stationary phase, the sample/mobile phase injector, and the chromatographic conditions (e.g. pressure, temperature, flow rate) to provide improved separation and resolution for more refined analysis, as will be appreciated by those of ordinary skill in the field.

The mobile phase reservoir is an integral component of any liquid chromatography system, and is particularly critical in an HPLC system. A reservoir in a liquid chromatography system must be capable of performing several functions. It must at least: (1) store the mobile phase; (2) act as the point from which the mobile phase is pumped into the column via the system's pump; (3) act as the site of mixing of the mobile phase to uniformity; (4) act as a reaction chamber in which adjustments to the mobile phase may be performed; (5) act as the site of degassing of the mobile phase; and (6) act as the site of sparging of the mobile phase.

From the chromatographer's point of view, the ability to rapidly mix the mobile phase to uniformity and the ability to utilize as much of the mobile phase as possible without introducing air bubbles into the system are critical features of a liquid chromatography mobile phase reservoir. The known reservoirs for use in a liquid chromatography system are either (1) flat-bottomed reservoirs, (2) reservoirs having a conical base and a single cavity subtending the conical base, or (3) reservoirs having a conical base similar to the Kontes reservoir but terminating in a 1–2 inch diameter flat surface rather than a cavity. In operation a stirrer is placed within the reservoir for mixing the mobile phase to uniformity. In addition, a pump inlet filter is also placed inside the reservoir for removing the mobile phase, and often a sparging device is also inserted to allow for helium sparging. The flat-bottomed reservoirs do not have any cavities, and while they provide good mixing, they require extra care in use in order to avoid interference with the stirrer by the pump inlet filter and the sparging device. Furthermore, these reservoirs must be tilted in order to utilize as much mobile phase as possible, and this procedure is dangerous when volatile or toxic chemicals are used as the mobile phase. Moreover, when the liquid level in these reservoirs falls low enough to expose some of the pump inlet filter to the air or gaseous phase in the reservoir, air bubbles will enter the tubing leading to the pump. Air bubbles cause problems for the pump valves and for the detection downstream from the HPLC column, and are incompatible with an efficient HPLC system.

The known reservoirs having the conical base and a single cavity increase the amount of the mobile phase removed from the reservoir (without resorting to dangerous tilting) compared to the flat-bottomed reservoirs. However, a significant drawback is that mixing is minimal. In these single cavity reservoirs, the cavity holds both a magnetic stirrer and a pump inlet filter. One disadvantage of this single cavity design is that only minimal mixing action for the mobile phase is achieved, even at high stirrer rpms (e.g., 1000 rpm), due to interference from the pump inlet filter and due to the spatial separation of the stirrer from the majority of the mobile phase located in the main chamber of the reservoir. This spatial separation or distance between the majority of the mobile phase and the stirrer is caused by the position of the stirrer at the bottom of the cavity under the inlet filter. For example, a pH adjustment in a typical conical, single cavity reservoir can take 30–60 minutes. Eliminating the cavity but retaining the conical base overcomes the spatial separation problem and improves mixing, but the pump inlet filter must be positioned high up enough on the conical slope to avoid interference with the stirrer. This inlet filter position increases the volume of mobile phase that cannot be pumped out of the reservoir without introducing air bubbles into the system.

SUMMARY OF THE INVENTION

The present invention relates to the structure of a reservoir for retaining the liquid or mobile phase used in a liquid chromatography system. The structure of the reservoir allows for rapid uniform mixing and maximum utilization of the mobile phase solution. The reservoir serves as the site from which the mobile phase is pumped into the liquid chromatography system's column.

In one embodiment of the present invention the reservoir comprises a mouth or opening at the top which allows for ingress and egress of the mobile phase. A main or first chamber of the reservoir makes up the bulk of the structure and contains the majority of the mobile phase solution. The base of the first chamber is sloped down and in toward the center of the reservoir, and in a preferred embodiment the slope is at an angle of approximately 2°–5°. The sloping base contains two apertures, the first aperture being slightly larger in diameter than the second aperture. The first aperture is located in the center of the base, with the second eccentrically positioned.

A cylindrical first cavity subtends the base of the reservoir and is in fluid connection with the first aperture. The first, centrally located cavity is adapted to receive a stirrer for mixing the mobile phase. In a preferred embodiment, the stirrer is a magnetic stirrer for obtaining maximum mixing of the liquid mobile phase in the reservoir's main or first chamber, and the volume of the stirrer approximates as closely as possible the volume of the first cavity. The placement of the stirrer in the first cavity, the slight downward slope of the base in toward the center of the reservoir, and the fluid connection of the main or first chamber of the reservoir with the first cavity via the first aperture combine to maximize utilization of the liquid mobile phase and minimize introduction of bubbles downstream from the reservoir, as will be discussed in greater detail below.

Furthermore, the placement of the stirrer in a cavity centrally positioned allows for maximum mixing of the mobile phase at 1000 rpm, so that pH adjustments and other changes in the composition or properties of the mobile phase is accomplished within minutes. The greater height of the stirrer compared to the depth of the stirrer cavity ensures that the blades of the stirrer extend directly into the main body of the stored mobile phase, and this ensures that the blades exert a stirring effect which closely approaches their maximum.

Also subtending the base of the reservoir, and in fluid connection with the second aperture, is a second cylindrical cavity adapted to receive a pump inlet filter. The pump inlet filter is connected to the liquid chromatography system's pump via a tube or hose and serves to provide a means to remove the liquid mobile phase contained in the reservoir and to filter the mobile phase prior to injection into the chromatography column via the pump and injector. The placement of the pump inlet filter in the second cavity, the slight downward slope of the base in toward the center of the reservoir, and the fluid flow communication of the main or first chamber of the reservoir with the second cavity via the second aperture combine to allow for efficient utilization of the liquid mobile phase and minimization of bubbles in the system downstream from the reservoir as discussed in the next paragraph.

In the preferred embodiment of the invention the first and second cavities are in fluid communication with one another via a hollow connecting tube subtending the base of the reservoir. This arrangement provides maximum utilization of the liquid mobile phase and effective minimization of bubbles downstream from the reservoir. The gradual slope of the base toward the center of the reservoir ensures that virtually all of the mobile phase enters the first cavity from the main or first chamber. The connection between the two cavities allows the stirrer to force virtually all of the liquid mobile phase to pass from the stirrer cavity to the inlet filter cavity by gravity flow when the liquid level in the reservoir has dropped below the entrance apertures of the two cavities. This allows the pump inlet filter to send virtually all of the liquid mobile phase out of the reservoir and into the chromatography column. The pump inlet filter is presented with a constant stream of uniformly mixed liquid mobile phase until essentially all of the mobile phase in the reservoir is exhausted. In this manner, the likelihood of air entering the pump inlet line is significantly lessened, and therefore, there is a decreased likelihood of disruptions in pump flow and pressure in the chromatography system. These advantages are further enhanced by the close approximation of the volume of the stirrer to the volume of the cavity so that virtually all of the mobile phase contained in the reservoir (including the stirrer and inlet filter cavities) is utilized before the pump inlet filter is exposed to air.

An annular skirt is connected to the bottom of the first or main chamber around the periphery of the base of the reservoir as a means of support for the reservoir. The skirt extends downward, approximately ¼ inch lower than the bottom of the first and second cavities, and contains a single small hole or degassing vent as a means to allow egress of air from the space beneath the base of the reservoir in the event the reservoir is placed in an ultrasonic bath for degassing.

In an alternative embodiment, the sloping base contains a single large aperture and cavity, with a partition extending across the diameter of the cavity which subdivides the cavity into two hemicylindrical portions. The partition does not extend to the bottom of the cavity, or is in some way incomplete, and accordingly, there is a fluid connection between the two portions of the cavity created by the partition. One of the two portions of the cavity holds a magnetic stirrer, the other a pump inlet filter, and the fluid connection between the stirrer portion and the filter portion provides enhanced mobile phase utilization with reduced air bubble introduction in the HPLC system downstream from the reservoir. The stirrer is able to function without causing excessive movement of the pump inlet filter, and the slope of the base toward the cavity allows virtually all of the mobile phase to flow into the cavity. The fluid connection between the two bottom portions of the cavity allows the mobile phase trapped in the stirrer portion of the cavity to flow by gravity to the inlet filter portion of the cavity when the mobile phase level drops below the top of the partition, thereby improving mobile phase utilization and reducing the likelihood of air bubbles being introduced into the system downstream from the reservoir. The partition may be curved so as to better accommodate the circular shape and rotary motion of the stirrer.

An annular skirt is connected to the bottom of the first or main chamber around the periphery of the base of the reservoir as a means of support for the reservoir. The skirt extends downward, approximately ¼ inch lower than the bottom of the single cavity, and contains a single small hole or degassing vent as a means to allow egress of air from the space beneath the base of the reservoir in the event the reservoir is placed in an ultrasonic bath for degassing.

BRIEF DESCRIPTION OF THE DRAWINGS

FIG. 1 is a schematic illustration of a liquid chromatography system including the mobile phase reservoir of the present invention.

FIG. 2 is a top perspective view of the mobile phase reservoir of the present invention.

FIG. 3 is a left side elevational view of the mobile phase reservoir of the present invention.

Figure 4:
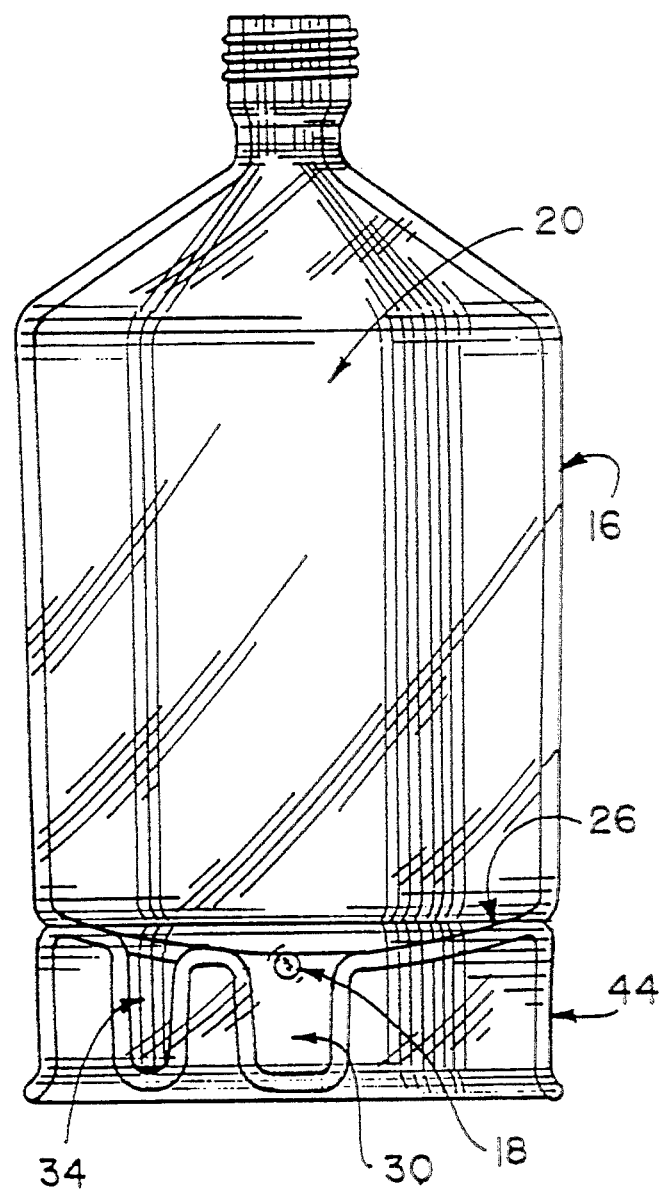
FIG. 4 is a left side elevational view of the mobile phase reservoir of the present invention showing the two cavity embodiment without a connecting tube.

While the invention is susceptible to various modifications and alternative forms, specific embodiments thereof have been shown by way of example in the drawings and will herein be described in detail. It should be understood, however, that the invention is not intended to be limited to the particular forms disclosed. On the contrary, the applicant's intention is to cover all modifications, equivalents, and alternatives failing within the spirit and scope of the invention as defined by the appended claims.

DETAILED DESCRIPTION OF THE INVENTION

Throughout the following detailed description reference is made to FIGS. 1-5 of the drawings, wherein like reference characters refer to like elements in all views.

FIG. 1 shows a schematic illustration of a liquid chromatography system. The mobile phase reservoir 16 of the present invention is placed amp a stirring unit 1 which drives a magnetic stirrer 2 inserted into the first cavity 30 of the mobile phase reservoir 16. A pump inlet filter 4 is placed in the second cavity 34 of the mobile phase reservoir 16, and the pump inlet filter 4 acts as the site of egress of the mobile phase from the mobile phase reservoir 16 as the pump 6 draws the mobile phase into the liquid chromatography system. The pump 6 then pumps the mobile phase to the injector 8 which injects the mobile phase and a sample into the column 10. The mobile phase then moves into the detector 12 and a recorder 14 analyzes the signal from the detector 12. Of course, during actual operation the reservoir 16 would have a cap (not shown).

Referring to FIG. 2 and FIG. 3, the mobile phase reservoir 16 is shown. A mouth 18 provides an opening into the main or first chamber 20 of the mobile phase reservoir 16. The mouth 18 provides for ingress and egress of the mobile phase and the outside wall 22 of the mouth 18, in a preferred embodiment of the invention, possesses threads 24 so that an appropriate cap can be screwed over the mouth 18 when necessary or appropriate for the use of the mobile phase reservoir 16.

FIG. 3 is a left side elevational view of the mobile phase reservoir 16 and shows the gradual downward slope of the base 26 of the main or first chamber 20 toward the center of the mobile phase reservoir 16. In a preferred embodiment of the invention there is located at the center of the base 26 a first aperture 28, the center of the first aperture 28 being substantially identical to the center of the base 26 of the main or first chamber 20, as shown in FIG. 2. The first aperture 28 allows for insertion of a plastic coated magnetic stirrer 2 into a cylindrical first cavity 30 which as can be seen in FIG. 3 subtends the base 26 of the main or first chamber 20 of the mobile phase reservoir 16, and which is in fluid communication with the main or first chamber 20 of the mobile phase reservoir 16 via the first aperture 28.

As can be seen in FIG. 2, the base 26 of the main or first chamber 20 also contains a second aperture 32 which allows for insertion of a pump inlet filter 4 or similar apparatus into a second cavity 34. As is shown in FIG. 3, the second cavity 34 subtends the base 26 of the main or first chamber 20 of the mobile phase reservoir 16. The second cavity 34 is in fluid communication with the main or first chamber 20 via the second aperture 32, and provides for maximum utilization of the mobile phase by allowing the final amounts of the mobile phase to collect in the bottom of the second cavity 34 so that the pump inlet filter can remove virtually all of the mobile phase so that none is wasted by being left in the mobile phase reservoir 16.

In a preferred embodiment of the invention, and as can be seen in FIG. 2, the first cavity 30 and the second cavity 34 are in fluid communication with one another via a hollow connecting tube 36 subtending the base 26 of the first chamber 20 of the mobile phase reservoir 16. As can be seen further in FIG. 2, in a further preferred embodiment the hollow connecting tube 36 opens into the wall 38 of the first cavity 30 and into the wall 40 of the second cavity 34 at the lowest points practicable so that all fluid collecting in the bottom of the first cavity 30 drains by gravity flow into the second cavity 34. This ensures that virtually all of the residual liquid mobile phase in the reservoir is available in the second cavity 34 for removal from the mobile phase reservoir 16 by the pump inlet filter 4. This goal is also furthered by the slope of the base 26 toward the center of the mobile phase reservoir 16 which allows for maximum drainage of the mobile phase held in the main or first chamber 20 into the first cavity 30.

Connected to the bottom of the main or first chamber 20 of the mobile phase reservoir 16, around the periphery 42 of the base 26 is an annular skirt 44 which serves as a means of support for the mobile phase reservoir 16. As is shown in FIG. 3, the bottom 46 of the annular skirt 14 subtends the bottoms of the first cavity 30 and the second cavity 34. The annular skirt 44 contains a hole or degassing vent 48 which allows air, which can be trapped inside the annular skirt 44 when the mobile phase reservoir 16 is placed in an ultrasonic degassing bath, to escape.

In the preferred embodiment, the first cavity 30 is centrally located and larger than the second cavity 34 which is eccentrically located. It will be understood by those of ordinary skill in the art that the size and position of the cavities can be changed to meet design considerations or operating requirements without departing from the scope of the present invention.

In an alternative embodiment shown in FIG. 4, the reservoir 16 is identical to that shown in FIGS. 2 and 3 except that the connecting tube 36 is removed. This reservoir 16 provides many of the same advantages of the reservoir 16 of FIGS. 2 and 3 except for the removal of the mobile phase remaining on the bottom of the cavity 30. Yet this dual cavity reservoir 16 provides rapid and uniform mixing of the mobile phase.

Figure 5:
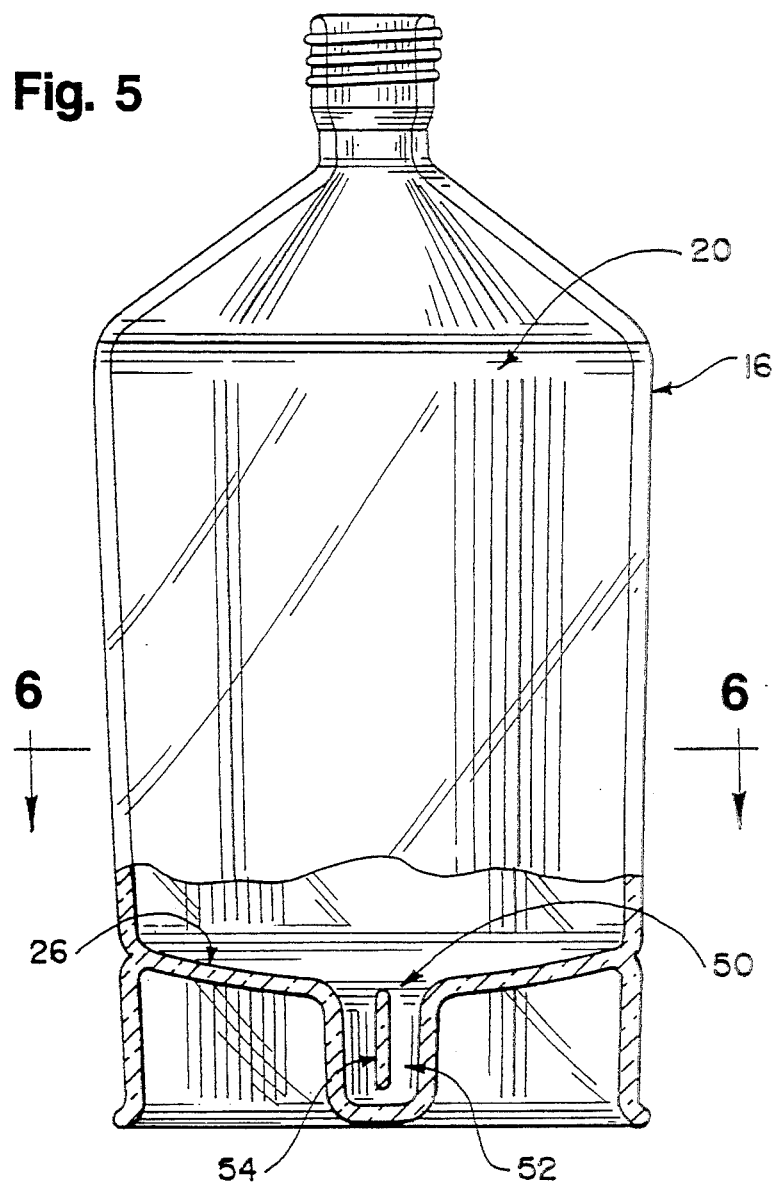
FIG. 5 is a front elevational view of the single cavity mobile phase reservoir of the present invention.
Figure 6:
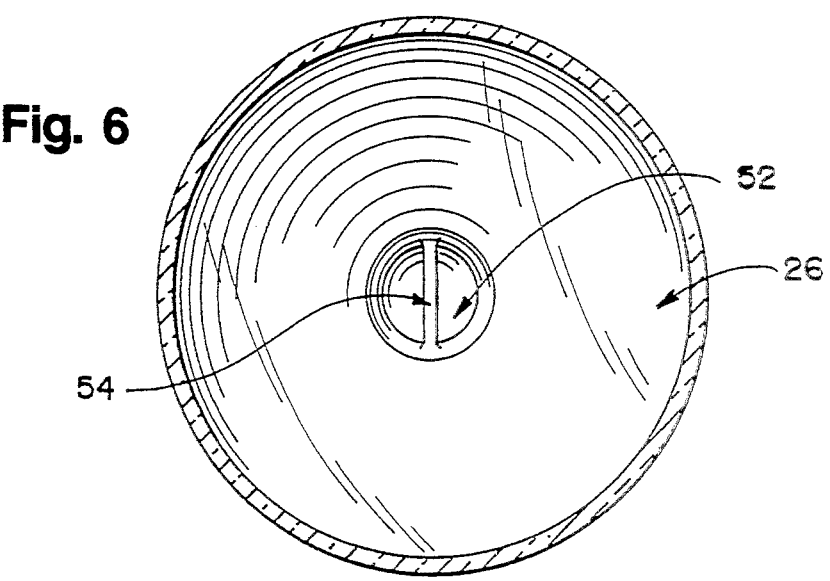
FIG. 6 is a top view of the single cavity mobile phase reservoir of the present invention, showing the portion of the reservoir below line 4—4 shown in FIG. 4.

An alternative embodiment of the mobile phase reservoir 16 is shown in FIGS. 5 and 6. In this alternative embodiment, a single aperture 50 is located at the center of the base 26, as shown in FIG. 5. The aperture 50 allows for fluid communication with a cavity 52 subtending base 26 of the main or first chamber 20 of the mobile phase reservoir 16.

As is shown in FIGS. 5 and 6, the cavity 52 is subdivided by a partition 54 into halves, although the partition 54 could create subcavities of unequal sizes or nonequivalent shapes, depending upon design considerations. In one embodiment, the partition 54 extends fully across the diameter of the cavity 52, as shown in FIG. 6 but does not extend to the bottom of the cavity 52, as shown in FIG. 5. In this manner fluid communication between the subcavities is maintained while preventing interference with a pump inlet falter (not shown) placed in one subcavity by a magnetic stirrer (not shown) placed in the other subcavity. Many variations of the partition 54 can be used to form two cavities and provide fluid communication between them. For example, partition 54 could go all the way to the bottom of the cavity but have holes through it to provide fluid communication. In another example, the partition 54 could extend only partially across the diameter of the cavity allowing fluid communication around one side. Any of these, as well as other modifications of the partition 54, come within the scope of the present invention. Many alternative embodiments are envisioned incorporating partitions of a variety of forms, all resulting in subdivision of the cavity 52 into two fluidly connected subcavities. As an alternative, the partition 54 could extend completely to the bottom of the cavity 52 thereby forming two separate cavities. This would be similar in operation and function to the two cavity reservoir without the connecting tube as shown in FIG. 4.

As described above, the present invention discloses the structure of a reservoir for use in a liquid chromatography system. The reservoir comprises a mouth or opening for ingress and egress of the mobile phase, a main chamber for containing the majority of the mobile phase, and in a preferred embodiment, a conical shaped base for the first chamber having a first centrally positioned aperture and a second eccentrically positioned smaller aperture, a first cavity subtending the conical shaped base and in fluid communication with the main chamber through the first aperture, a second cavity subtending the conical shaped base and in fluid communication with the main chamber through the second aperture, a hollow tube connecting said first and second cavities and a skirt portion extending downward from the main chamber for supporting the reservoir upon a flat surface. The reservoir receives a stirrer positioned in the first cavity for maximizing the mixing of the mobile phase and receives a pump filter in the second cavity for enabling substantially all of the mobile phase to be removed from the reservoir without an appreciable risk of the introduction of air bubbles in the system downstream from the reservoir. In an alternative embodiment the conical shaped base possesses a single aperture, with a single cavity subtending said base and in fluid communication with the main chamber, the single cavity being subdivided by a partition designed to allow fluid communication between the subcavities created by the partition. It will be recognized by those skilled in the art that the invention is susceptible to various alternative forms and modifications, and it is not intended to be limited to the particular forms disclosed.

What is claimed is:

1. A reservoir for the mobile phase of a liquid chromatography system, the reservoir comprising:
   a mouth for receiving said mobile phase;
   a first chamber positioned below said mouth for containing the majority of said mobile phase;
   a sloping base forming the bottom of said first chamber and containing first and second apertures;
   a first cavity subtending said base and in fluid connection with said first aperture;
   said first cavity being sized and dimensioned to receive a stirrer for mixing said mobile phase in said first chamber;
   a second cavity subtending said base and in fluid connection with said second aperture;
   said second cavity being sized and dimensioned to receive a pump inlet filter for removing said mobile phase from said reservoir;
   said first and second cavity being sized and dimensioned to facilitate removal of substantially all of said mobile phase from said first chamber before the pump inlet filter is exposed to air; and
   a support means connected to said first chamber for maintaining said reservoir upright.

2. The reservoir of claim 1 further comprising a hollow tube subtending said base and connecting said first cavity and said second cavity in fluid communication with one another.

3. The reservoir of claim 1 wherein said first aperture is located at substantially the center of said sloping base.

4. The reservoir of claim 3 wherein said second aperture is located eccentrically with respect to said first aperture.

5. The reservoir of claim 4 wherein said support means comprises an annular skirt connected to said first chamber and extending downward to contact a surface for supporting said reservoir upright.

6. The reservoir of claim 5 wherein said annular skirt further comprises a degassing vent.

7. The reservoir of claim 6 wherein the slope of said sloping base comprises an angle of approximately 2°–5° downward toward the center of said first cavity.

8. A reservoir for the mobile phase of a liquid chromatography system, the reservoir comprising:
   a mouth for receiving said mobile phase;
   a first chamber positioned below said mouth for containing the majority of said mobile phase;
   a sloping base forming the bottom of said first chamber and containing first and second apertures, said first aperture being located at substantially the center of said sloping base and said second aperture being located eccentrically with respect to said second aperture;
   a first cavity subtending said base and in fluid connection with said first aperture;
   said first cavity being sized and dimensioned to receive a stirrer for mixing said mobile phase in said first chamber;
   a second cavity subtending said base and in fluid connection with said second aperture;
   said second cavity being sized and dimensioned to receive a pump inlet filter for removing said mobile phase from said reservoir;
   a hollow tube subtending said base and connecting said first cavity and said second cavity in fluid connection with one another;
   said first and second cavity being sized and dimensioned to facilitate removal of substantially all of said mobile phase from said first chamber before the pump inlet filter is exposed to air; and
   a support means connected to said first chamber for maintaining said reservoir upright, said support means comprising an annular skirt connected to said first chamber and extending downward to contact a surface for supporting said reservoir upright.

9. The reservoir of claim 8 wherein said annular skin further comprises a degassing vent.

10. A reservoir for the mobile phase of a liquid chromatography system, the reservoir comprising;
    a mouth for receiving said mobile phase;
    a first chamber positioned below said mouth for containing the majority of said mobile phase;
    a sloping base forming the bottom of said first chamber and containing an aperture;
    a cavity subtending said base and in fluid connection with said aperture, a partition dividing said cavity into first and second subcavities;
    said first subcavity being sized and dimensioned to receive a stirrer for mixing said mobile phase in said first chamber;

said second subcavity being sized and dimensioned to receive a pump inlet filter for removing said mobile phase from said reservoir;

said first and second cavity being sized and dimensioned to facilitate removal of substantially all of said mobile phase from said first chamber before the pump inlet filter is exposed to air; and a support means connected to said first chamber for maintaining said reservoir upright.

11. The reservoir of claim 10 wherein said partition allows fluid communication between said first and second subcavities.

12. The reservoir of claim 11 wherein said aperture is located at substantially the center of said sloping base.

13. The reservoir of claim 11 wherein said aperture is located eccentrically with respect to the center of said sloping base.

14. The reservoir of claim 11 wherein said support means comprises an annular skirt connected to said first chamber and extending downward to contact a surface for supporting said reservoir upright.

15. The reservoir of claim 14 wherein said annular skirt further comprises a degassing vent.

* * * * *